(12) United States Patent
Friedlander

(10) Patent No.: US 8,377,716 B2
(45) Date of Patent: Feb. 19, 2013

(54) METHOD FOR EFFICIENT AND PRECISE TRANSFER OF LIQUIDS

(76) Inventor: Thomas Friedlander, Rye Brook, NY (US)

( * ) Notice: Subject to any disclaimer, the term of this patent is extended or adjusted under 35 U.S.C. 154(b) by 0 days.

(21) Appl. No.: 13/527,374

(22) Filed: Jun. 19, 2012

(65) Prior Publication Data

US 2012/0255970 A1    Oct. 11, 2012

Related U.S. Application Data

(62) Division of application No. 12/767,900, filed on Apr. 27, 2010, now Pat. No. 8,236,256.

(51) Int. Cl.
*G01N 1/10* (2006.01)
(52) U.S. Cl. .................. 436/180; 436/54; 422/501
(58) Field of Classification Search .................. 436/180, 436/54; 422/501–524; 222/14, 21, 82, 98–100, 222/173–174
See application file for complete search history.

(56) References Cited

U.S. PATENT DOCUMENTS

| | | | |
|---|---|---|---|
| 3,918,910 A | 11/1975 | Soya et al. | |
| 5,435,197 A | 7/1995 | Telimaa et al. | |
| 5,650,122 A * | 7/1997 | Harris et al. | 422/81 |
| 5,665,312 A * | 9/1997 | Sperber et al. | 422/81 |
| 5,897,034 A | 4/1999 | Sewell | |
| 6,254,832 B1 | 7/2001 | Rainin et al. | |
| 6,431,015 B1 | 8/2002 | Hodac et al. | |
| 6,579,497 B2 | 6/2003 | Woodward | |
| 6,627,157 B1 * | 9/2003 | Doktycz et al. | 422/503 |
| 6,749,812 B2 | 6/2004 | Cronenberg et al. | |
| 6,814,936 B1 | 11/2004 | Enhorning | |
| 6,887,429 B1 * | 5/2005 | Marshall et al. | 422/81 |
| 6,923,938 B2 | 8/2005 | Cote et al. | |
| 7,182,912 B2 | 2/2007 | Carey et al. | |
| 7,547,556 B2 | 6/2009 | Hunter et al. | |
| 7,638,023 B2 * | 12/2009 | Marquant | 204/403.02 |
| 7,687,269 B2 * | 3/2010 | Kautz et al. | 436/52 |
| 7,972,576 B2 * | 7/2011 | Langer et al. | 422/501 |
| 7,988,934 B2 | 8/2011 | Balmer | |
| 8,124,413 B2 * | 2/2012 | Stanley et al. | 436/53 |
| 2001/0016359 A1 * | 8/2001 | Bryning et al. | 436/180 |
| 2001/0034067 A1 * | 10/2001 | Dales et al. | 436/180 |
| 2002/0012613 A1 | 1/2002 | Scordato et al. | |
| 2003/0087454 A1 * | 5/2003 | Schultz et al. | 436/161 |
| 2003/0223915 A1 * | 12/2003 | Sagstetter | 422/103 |
| 2005/0079105 A1 * | 4/2005 | Hunter et al. | 422/100 |
| 2005/0118069 A1 | 6/2005 | Solotareff et al. | |
| 2005/0244303 A1 | 11/2005 | Ingenhoven et al. | |
| 2007/0025882 A1 | 2/2007 | Zuppiger et al. | |

* cited by examiner

*Primary Examiner* — Brian R Gordon
(74) *Attorney, Agent, or Firm* — UConn IP Law Clinic; Lilly Neff; Yang Gao

(57) ABSTRACT

A method for aspirating and/or dispensing liquids. The method includes preselecting a volume of liquid to be aspirated and/or dispensed; aspirating and/or dispensing the liquid through an actuator by extruding tubing in a spool included in a cartridge inside of a housing and aligning the extruded tubing with a fixed tip protruding partially out of the housing such that liquid can be aspirated and/or dispensed by a pump included in the actuator.

3 Claims, 6 Drawing Sheets

METHOD FOR EFFICIENT AND PRECISE TRANSFER OF LIQUIDS

CROSS REFERENCE

This is a Continuation Application. U.S. patent application Ser. No. 12/767,900 filed on Apr. 27, 2010 incorporated entirely herein.

FIELD OF INVENTION

This invention relates generally to a method for transferring liquids of reagents and samples that optimizes accuracy and efficiency.

BACKGROUND OF THE INVENTION

Pipetting systems are widely used in the pharmaceutical industries, as well as in industries dealing in cosmetics, food and beverage production. These systems are also used in clinical research applications. These systems are used to aspirate and dispense relatively small and/or preselected volumes of liquids from one receptacle to another. Conventional pipetting systems generally include a housing that comprises a piston and a plunger to enable dispensing and aspiring of liquids. A rigid plastic tip is usually also attached to the pipette, at one end, to enable the transfer and to prevent contamination of liquids by successive samples, often disposable plastic tips are used. Unfortunately, conventional pipetting systems have several shortcomings and problems associated with their use.

One problem associated with the use of these systems deal with the operation of transferring liquids from one receptacle into another. Operations of conventional pipettes need to be manually performed by applying force to the plunger head, usually with a thumb or a finger, in order to actuate the piston. Even if the plunger can be motorized, the user still needs to tightly grip the pipette, especially when mounting and removing the tip from the tip holder. Since repetitive and frequent operation of the pipette is required every day, continued use of these systems contributes to an increased risk of hand and shoulder injuries and may lead to other related ailments often associated with repetitive stress injuries.

A second problem associated with the use of conventional pipettes is the accuracy and range of volume that can be transferred with such devices. Precise measurements of liquids are difficult to achieve and different transfer of volumes in a wide range cannot be accomplished by a single device and therefore different devices and different corresponding tips have to often be utilized. Even then, accuracy is difficult to achieve using current disposable tips as they need to be made from rigid materials in order to allow for proper mounting of the tip to the device. Unfortunately, the mounting of such tips still leaves a large air gap between the piston of the device and the liquid being aspirated and/or dispensed. This gap subsequently affects the accuracy of the actual volume being transferred. The effect of inaccurate dispensation/aspiration is more significant and noticeable when small volumes of liquid are being transferred. As with regards to range of volume supported, the changing of the devices and/or their associated tips affects the overall labor and cost requirements which can burden the overall operation.

A related problem associated with using prior art pipettes that require disposable plastic tips is environmental concerns. As environmental awareness has increased, a great deal of attention is being paid to reducing the environmental impact by minimizing the need to utilize disposable plastic tips.

Consequently, it is desirable to have an improved apparatus and method which can overcome some of the problems associated with the prior art systems as enumerated.

SUMMARY OF THE INVENTION

The shortcomings of the prior art are overcome and additional advantages are provided through the provision of a device and related method for automatically aspirating and/or dispensing liquids with precision. The device, in one embodiment, comprises a housing having an opening at a lower end with a fixed tip protruding out of this lower end. It also comprises an interchangeable cartridge disposed inside the housing having a spool of plastic tubing such that one end of the tubing is positioned to align with the center of the fixed tip and an actuator. The actuator is enabled to automatically extrude part of the tubing so as to accommodate a preselected volume of liquid and aspirate and/or dispense the liquid through the extruded tubing. This embodiment further comprises a control circuit operable to drive the actuator. The control circuit has a plurality of power sources, actuateable control keys in electrical communication with the control circuit and enabled to preselect modes of operation and volumes of liquid to be aspirated and/or dispensed, a display for displaying numbers and/or alpha-numerical characters, and a memory component for storing data accessible by the control circuit to enable preselected operations.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION

Figure 1:
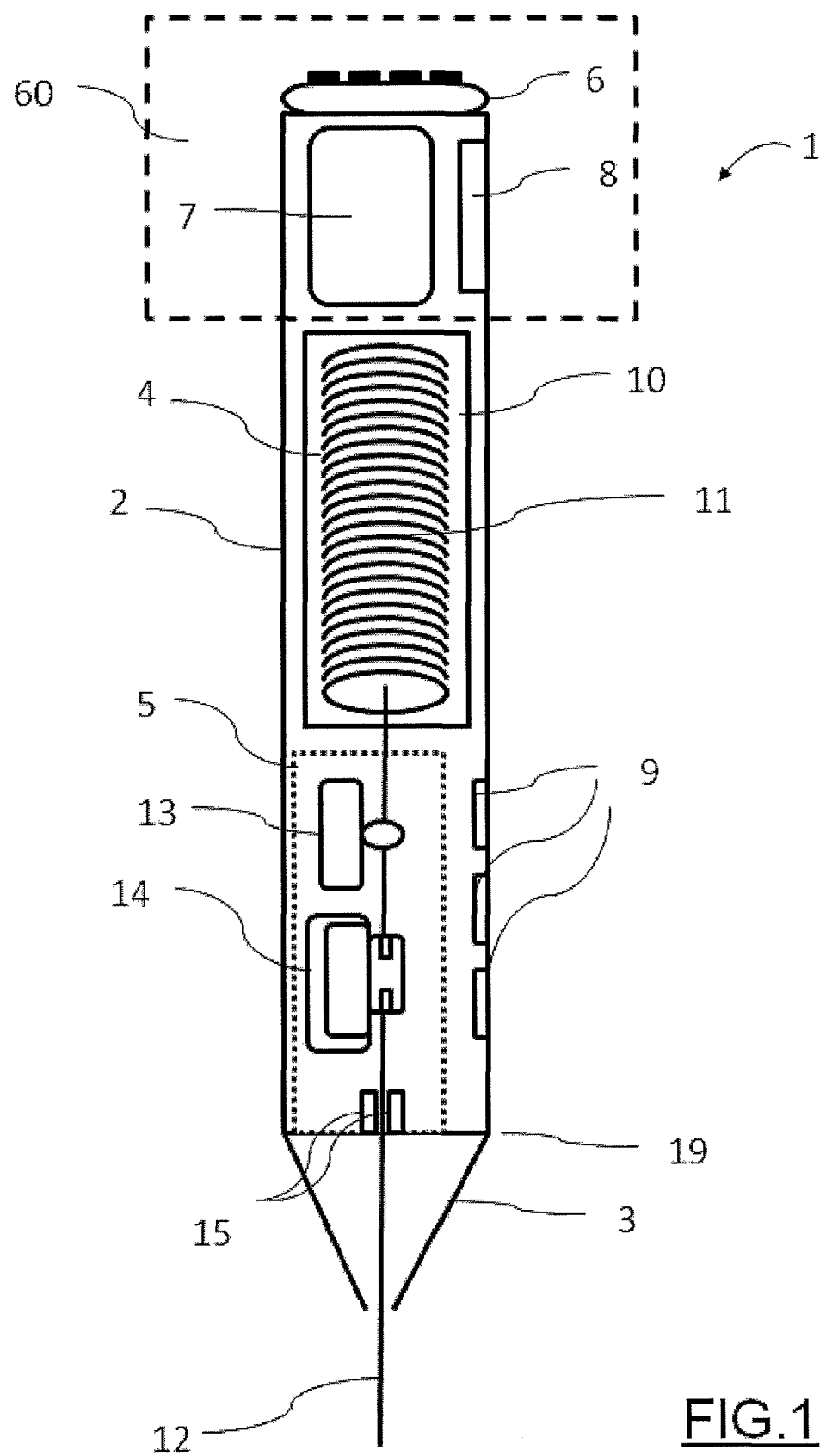
FIG. 1 is a schematic illustration providing a sectional view of one embodiment of the present invention.

FIG. 1 is a cross sectional depiction of one embodiment of the present invention illustrating a liquid transferring device as referenced by numeral 1. The liquid transferring device 1 comprises a housing 2 having an opening at its lower end 19. The housing shown in FIG. 1 has a generally cylindrical shape, however, other alternate shapes and structures can also be provided as known to those skilled in the art in alternative embodiments and the cylindrical shape of the housing 2 in FIG. 1 is only provided by way of example.

In one embodiment, as shown in FIG. 1, the lower end 19 of the housing 2 can further include a tip, preferably having a substantially conical shape or other such structure as known to those skilled in the art. In this embodiment, the conical shape is chosen to aid structural support to tubing that can be extruded, as is described latter in this specification. As shown, the conical tip is referenced by numeral 3. In this embodiment, the tip 3 is elongated in design, extending from the housing 2 such that the tip 3 generally protrudes out of the lower end 19.

The housing 2 also comprises a cartridge referenced as 4. In one embodiment, as shown the cartridge 4 is disposed at an opposing end from the tip 3. In a preferred embodiment, the cartridge 4 is an interchangeable cartridge which further comprises a holding frame 10 and one or more spool(s) of tubing 11, the spool(s) being disposed in the frame 10. The spool 11, in one embodiment, is positioned such that one end of the tubing in the spool 11 is enabled to align with and be extruded out of the conical tip 3, with the extruded portion shown by numerals 12. Tubing in spool 11 can have a variety of inner diameters selectively interchangeable depending on the desired volume of liquid to be handled. In addition, tubing in spool 11 can be fabricated of different materials in order to accommodate a range of materials and liquids that need to be transferred. For example, plastic tubing may be used in relation to a first material but such tubing may not be suitable to be used with certain type of concentrated acids and a material replacement needs to be made to handle the latter. In some embodiments of the invention the inner wall or surface of the tubing in spool 11 can be pretreated with selective reagents. For example, the tubing can be pretreated so as to provide pre-coating with antibodies or other materials as known to those skilled in the art. Pretreatment of tubing can provide a number of different advantages as appreciated by those skilled in the art. For example, pretreatment can minimize risk of contamination or alternatively can be used to reduce the number of processing steps required. The length of tubing can also be selective. The latter can easily replace the need for disposable tips such as used in traditional devices, with the added advantage of providing a continuous supply and adjustable length of tubing (and tips) and allowing a wide range of operations with a single device. The tubing in spool 11 is also able to be pressed to a flat form when rolled in the spool 11, and is able to form a tubular form when extruded.

Figure 3:
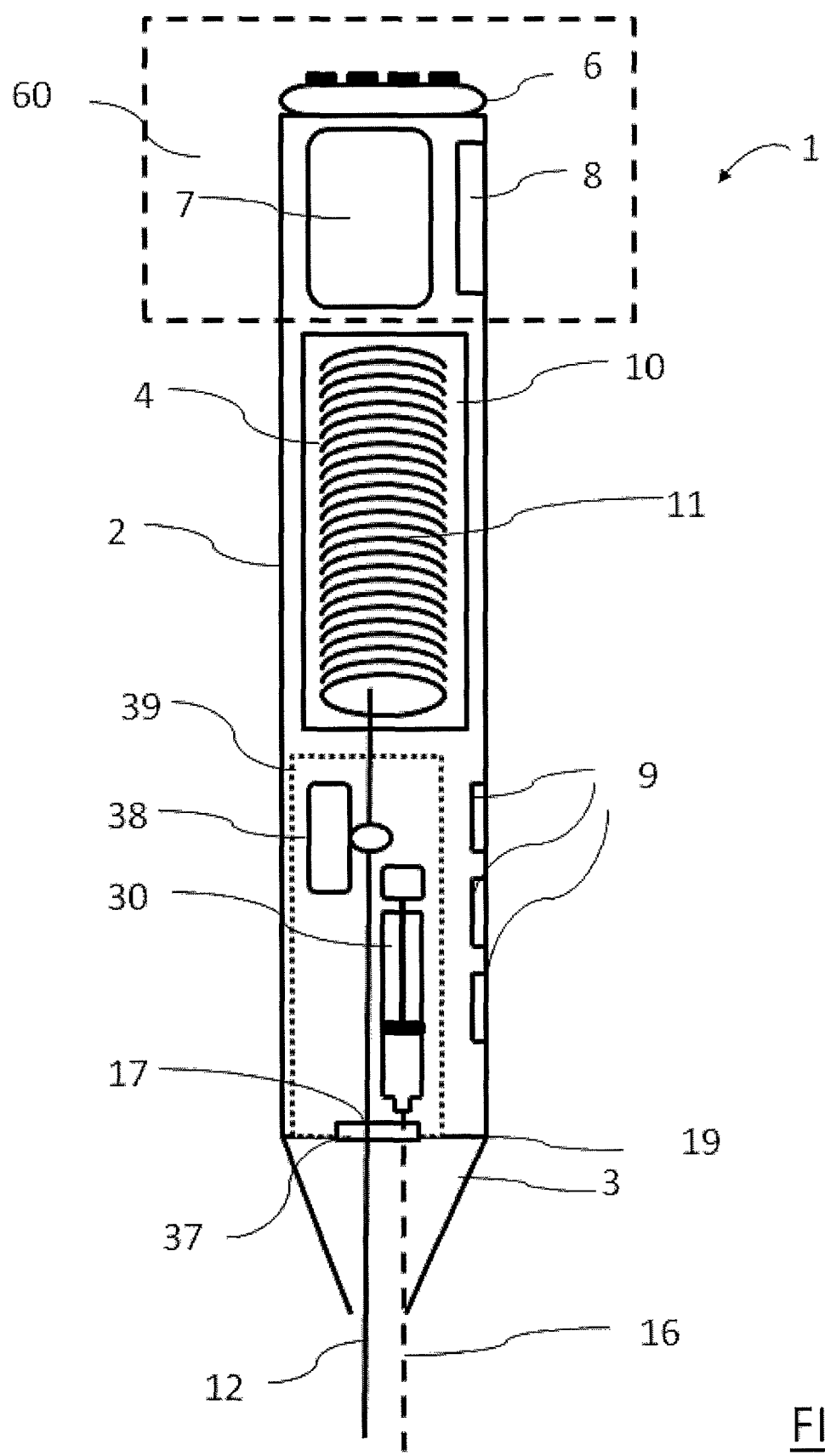
FIG. 3 is a schematic illustration providing a sectional view of an alternate embodiment of the present invention.

In the embodiment of FIG. 1, an actuator 5 is also provided and disposed in the housing 2 below the interchangeable cartridge 4. The actuator 5, in one embodiment can have a plurality of components. In FIG. 1 shown, the actuator 5 includes three components: namely a mechanism 13, a pump 14, and a cut-off component 15. Different components or additional ones can be used/substituted or removed in other environments. In the embodiment shown in FIG. 1, the pump 14 is a peristaltic pump. However, other types of pumps can be utilized as known by those skilled in the art in alternate embodiments. For example, as will be discussed later, in another embodiment as shown in FIG. 3, a syringe pump is provided. In FIG. 1 shown, mechanism 13 is enabled to automatically extrude a portion of tubing from spool 11. In one embodiment, the spool can then be dissected, cut, perforated, pinched etc. such that a desired amount of tubing length is extruded and at least a certain amount of the extruded portion is isolated and/or sealed off from the spool 11.

Figure 2:
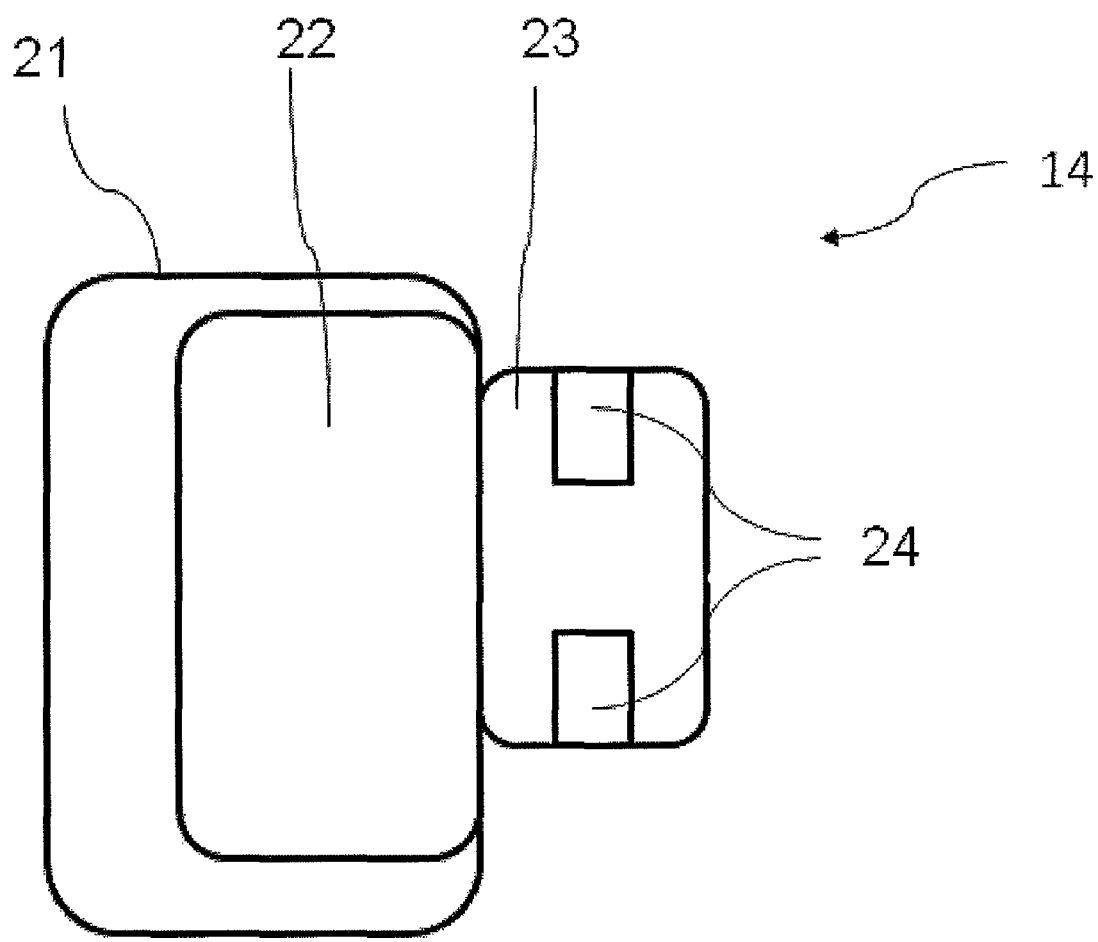
FIG. 2 is a more detailed illustration of the peristaltic pump as provided by the embodiment of FIG. 1.

FIG. 2 provides a cross sectional detailed view of the peristaltic pump 14 as used in conjunction with the embodiment as shown in FIG. 1. As shown in FIG. 2, the peristaltic pump 14 comprises a pump casing 21, a pump motor 22 disposed inside the pump casing 21, and a rotor 23 having one or more rollers 24 such that the portion of tubing to be extruded can become partially secured inside the rotor 23. The rollers 24 are enabled to move over the tubing which can be secured inside the rotor to aspirate and/or dispense a preselected volume of liquid (through the extruded tubing 12). Component 15 can then be retrofitted to dissect and/or seal the remainder of the extruded tubing as needed and disconnect it from the device as appropriate.

FIG. 3 provides a cross sectional view of an alternate embodiment of the present invention. The embodiment shown in FIG. 3 shares several common elements with the embodiment of FIG. 1 as discussed, and therefore some of the referenced numerals are reused as appropriate.

In the illustration of FIG. 3, however, an actuator 39 is disposed in the housing 2 below the interchangeable cartridge 4. This actuator is shown to also have a plurality of components; namely a mechanism 38, a syringe pump 30, and a component 37. Mechanism 38 is enabled to automatically extrude a portion of the tubing from the spool 11. In addition, component 37 is also enabled to cut off at least a portion of the extruded tubing 12 at a first position indicated by numerals 17, and if needed, ultimately move the cut-off portion of the extruded tubing to align with the pump 30, as appropriate, as indicated by numerals 16. Furthermore, in some embodiments, the cut-off portion of the tubing can also be sealed to the syringe pump 30 as needed.

Figure 4:
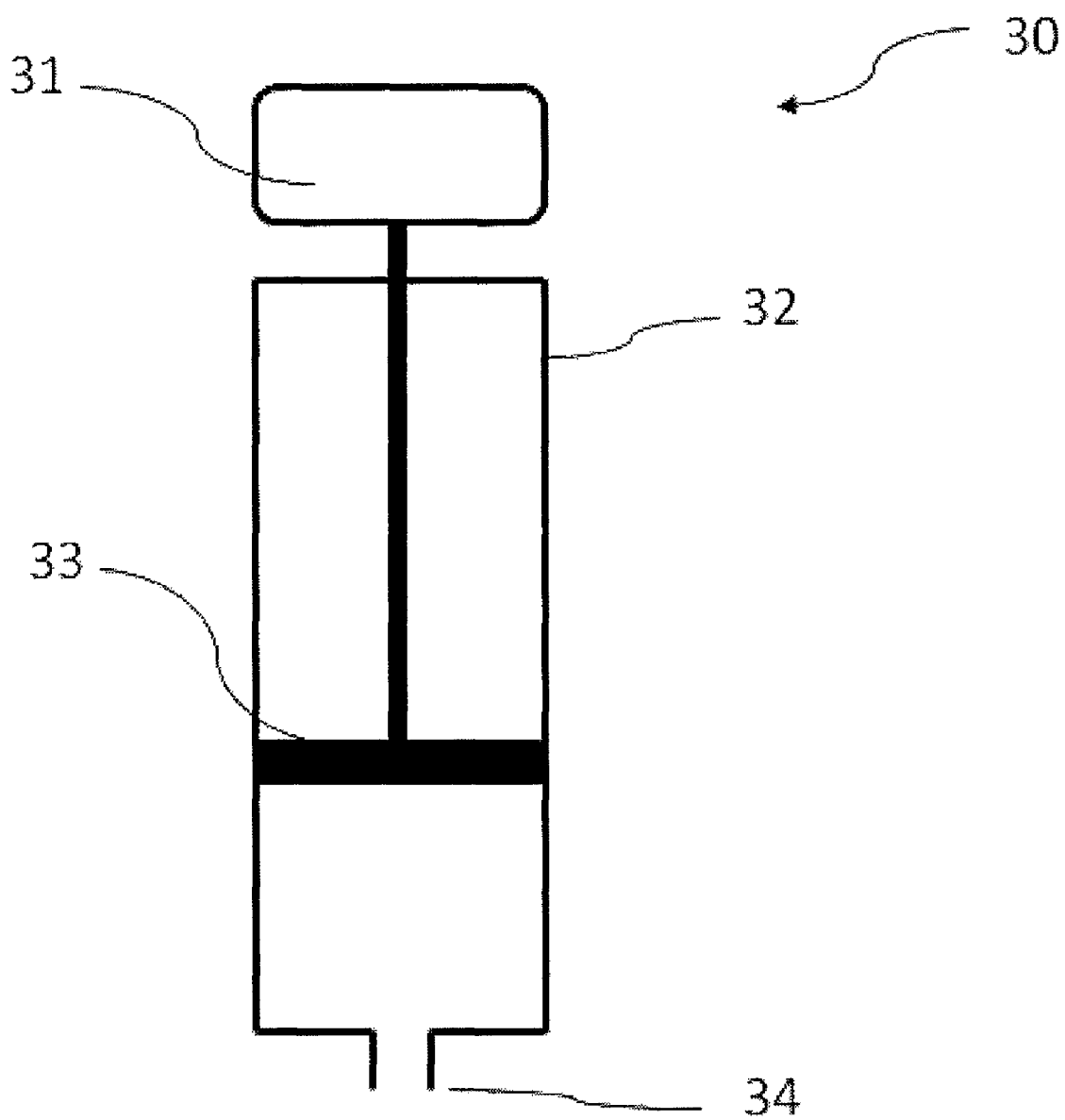
FIG. 4 is a more detailed illustration of the syringe pump as provided by the embodiment of FIG. 3.

FIG. 4 provides a cross sectional illustration of the syringe pump 30 as used in conjunction with the embodiment shown in FIG. 3 in more detail. As shown in FIG. 4, the syringe pump in this embodiment comprises additional components. In the figure shown, the syringe pump 30 includes a syringe driver 31, a barrel 32 having an orifice 34 at one end, and a plunger 33 received in a second end of the barrel 32. Once a portion of tubing in spool 11 is extruded by mechanism 38, component 37 dissects or cuts off at least a portion of the extruded tubing at a first position 17 and seals the cut-off tubing portion to the orifice 34, as indicated by 16. The plunger 33 moves along inside the barrel 32 to aspirate and/or dispense a preselected volume of liquid through tubing 16. Component 37 is also enabled to disconnect tubing 16 from the device as appropriate.

Figure 5:
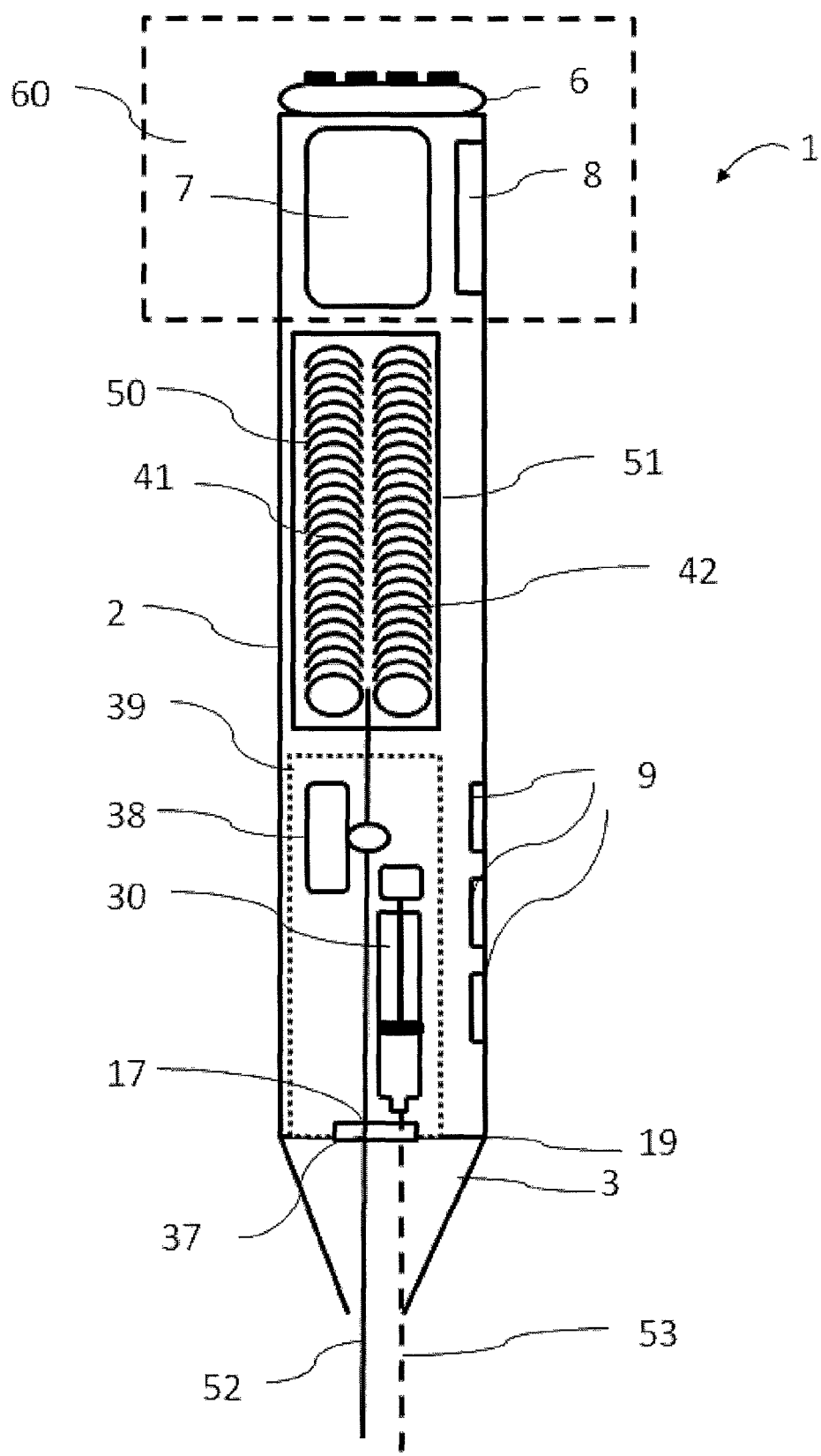
FIG. 5 is a sectional view illustration of another alternate embodiment of the present invention.
Figure 6:
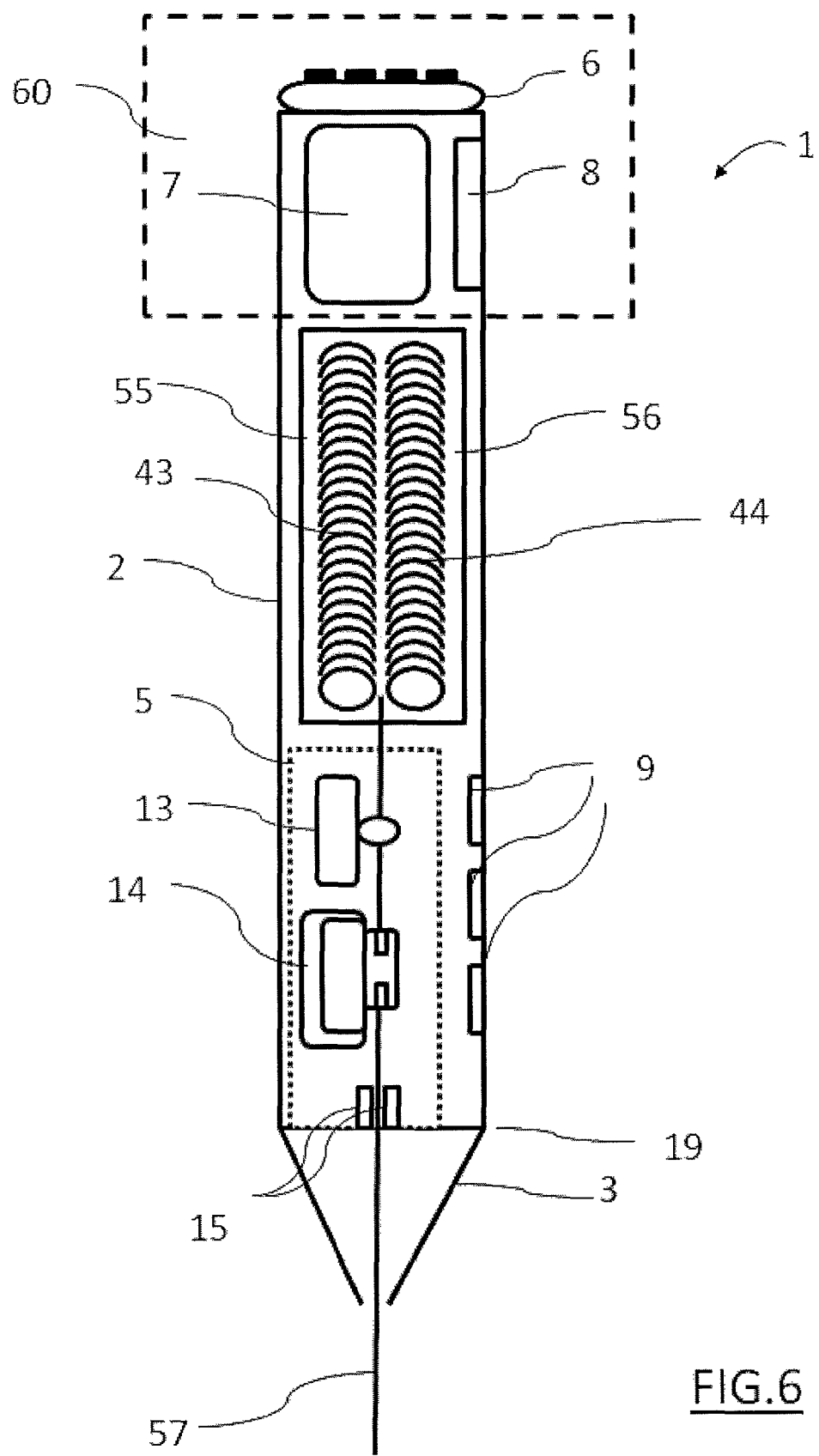
FIG. 6 is a sectional view illustration of yet another alternate embodiment of the present invention.

FIG. 5 and FIG. 6 provide alternate embodiments of the present invention. FIG. 5 and FIG. 6 share several common elements with the embodiments of FIG. 1 and FIG. 3, respectively, and therefore some of the referenced numerals are reused as appropriate. In the cross sectional illustration of the embodiment provided by FIG. 5, the interchangeable cartridge 50 has a holding frame 51 and a plurality of tubing spools that are disposed in the frame 51. Tubing in each spool can have a different inner diameter, length or be made of different materials or have a combination of all or some of the above mentioned characteristic variations. Alternatively one or more tubing can be pretreated with same or different coating of materials. The thickness of such coatings can also be selectively varied such that one spool may include a thin coating of a first substance and a second spool can include a thicker coating of the first or different substance. In the embodiment shown in FIG. 5, as way of example only two spools, 41 and 42 are illustrated. This is done to ease understanding but more spools can be provided in other embodiments as appreciated by those skilled in the art. In each case, the liquid amounts to be aspirated and/or dispensed can be transferred using a pump 30 such as the syringe pump as discussed in conjunction with the embodiments provided by FIG. 3 and FIG. 4.

In the cross sectional illustration of the alternate embodiment of FIG. 6, an interchangeable cartridge 55 has a holding frame 56. Two spools of tubing 43 and 44 are also provided in the frame 56. The embodiment of FIG. 6 is similar in operation to FIG. 5, except that a peristaltic pump 14 as discussed in conjunction with the embodiments provided by FIG. 1 and FIG. 2 is used.

In one embodiment of the present invention, the actuator 5 such as used in conjunction with FIGS. 1-6 can be driven by a control circuit generally shown by box 60 having a power source 7, a display 8, and a memory component 6. The control circuit 60 also includes and/or is in processing communication with actuateable control keys 9. In this embodiment the control keys 9 are disposed outside the general circuit box 60. However, alternate arrangements are possible in other embodiments. The memory component 6, the power source 7, the display 8, and the actuateable control keys 9 are in electrical communication with one other. The control keys 9 allow a user to preselect a range of volumes of liquid to be transferred. The keys 9 can also be used to preselect modes of operation, trigger certain preselected operations, such as aspirating or dispensing, or alternatively select among programs or user-defined operations, and/or to reset operations. In addition, in some embodiments, the time of aspirations and/or dispensations or intervals between aspiration(s) and/or dispensation(s) can be programmable to start or end at certain designated time or time intervals. Display 8 shows user-input commands and selections, or alternatively the status of the operations either in numbers and/or alpha-numerical characters. Information regarding the operation of the device is stored on the memory component 6, which is accessible by the control circuit 60.

In alternate embodiments, the control circuit as shown by box 60 can be a part of an automated system such as a computer or a computing system that includes one or more processors. In some embodiments, as appreciated by those skilled in the art, it is possible for the liquid transferring device to be connected to the automated system such that at a certain time, as preselected by user(s), one or more spools are disposed, if not already included in the device and then a preselected volume of liquids is either aspirated and/or dispensed automatically. This process can then be selectively repeated at selective preset intervals or at set times preselected by the user(s). The type of spool/tubing to be used can also be preselected such that different aspiration/dispensation processes are conducted automatically by spools having different diameters, materials, pretreatments and the like. The automated system or computer can also make a determination to insert or exchange spools of tubing as necessary for each dispensation or aspiration process to be conducted.

As per one embodiment, volumes of liquid to be aspirated and/or dispensed can be preselected by user(s) via the actuateable control keys 9. When a peristaltic pump 14 is included in the actuator, as is described in FIG. 1 and FIG. 6, mechanism 13 is initiated to extrude the tubing to a length able to accommodate the preselected volume and pinch the extruded tubing 12 once a desired length is extruded. In this way, the extruded tubing is isolated and sealed from the spool. The length to be extruded is calculated by the memory component 6 based on the preselected volume and the inner diameter of the tubing being extruded. The preselected volume of liquid is aspirated and/or dispensed by moving the rollers 24 over the tubing secured inside the rotor of the peristaltic pump. After transferring the liquid, the extruded tubing is disconnected from the device by component 15. Each above operation is triggered via the actuateable control keys 9. The display 8 allows a user to monitor the status of each operation and to also look up operating parameters for previous operations.

In another embodiment, in order to aspirate or dispense liquids using a syringe pump, as shown in FIG. 3 and FIG. 5, the volume of liquid to be aspirated and/or dispensed is preselected by user(s) via the actuateable control keys 9. Mechanism 38 is initiated to extrude the tubing to a length able to accommodate the preselected volume. The length to be extruded can be calculated, as per one embodiment, by the memory component 6 based on the preselected volume and inner diameter of tubing being extruded. The extruded tubing is cut off from the remaining spool by component 37 and the cut-off portion of the extruded tubing is sealed to the syringe pump at its orifice. The preselected volume of liquid is aspirated and/or dispensed by the movement of the plunger inside of the syringe pump. After transferring the liquid, the cut-off portion of the extruded tubing can be disconnected from the device by component 37. Similarly, each above operation is triggered via the actuateable control keys 9. The display 8 allows a user to monitor the status of each operation of the above process, and to look up operating parameters for previous operations.

While the invention has been described in accordance with certain preferred embodiments thereof, those skilled in the art will understand the many modifications and enhancements which can be made thereto without departing from the true scope and spirit of the invention, which is limited only by the claims appended below.

What is claimed is:

1. A method for aspirating and/or dispensing liquids, comprising:
   preselecting a volume of liquid to be aspirated and/or dispensed;
   aspirating and/or dispensing said liquid through an actuator by extruding tubing in a spool included in a cartridge inside of a housing of a device and aligning said extruded tubing with a fixed tip protruding partially out of said housing such that liquid can be aspirated and/or dispensed by a pump included in said actuator.

2. The method as set forth in claim 1 further comprises disconnecting said extruded tubing from said device.

3. A method for aspirating and dispensing liquids, comprising:
   preselecting a volume of liquid to be aspirated and/or dispensed;
   extruding automatically a length of tubing in a spool included in a cartridge to accommodate said preselected volume by an actuator disposed inside of a housing of a device;
   said actuator cutting off said extruded tubing from remaining tubing in said spool and substantially sealing said cut-off portion of said extruded tubing so as to be usable by a pump; said pump being disposed inside said housing;
   aspirating and/or dispensing said preselected volume by said pump; and disconnecting said cut-off portion of said extruded tubing from said device.

* * * * *